US012657700B2

(12) United States Patent

Kasahara et al.

(10) Patent No.: US 12,657,700 B2

(45) Date of Patent: Jun. 16, 2026

(54) ULTRASOUND TIME-SERIES DATA PROCESSING DEVICE AND ULTRASOUND TIME-SERIES DATA PROCESSING PROGRAM

(71) Applicant: FUJIFILM Healthcare Corporation, Kashiwa (JP)

(72) Inventors: Eiji Kasahara, Chiba (JP); Katsunori Asafusa, Chiba (JP); Tomoaki Chono, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 289 days.

(21) Appl. No.: 18/138,669

(22) Filed: Apr. 24, 2023

(65) Prior Publication Data

US 2023/0368376 A1 Nov. 16, 2023

(30) Foreign Application Priority Data

May 16, 2022 (JP) ................................. 2022-080338

(51) Int. Cl.
*G06T 7/00* (2017.01)
*A61B 8/00* (2006.01)
(Continued)

(52) U.S. Cl.
CPC .............. *G06T 7/0012* (2013.01); *G06T 5/70* (2024.01); *G16H 30/40* (2018.01); *A61B 8/5269* (2013.01);
(Continued)

(58) Field of Classification Search
CPC ..................... G06T 7/0012; G06T 5/70; G06T 2207/10132; G16H 30/40; G16H 30/20;
(Continued)

(56) References Cited

U.S. PATENT DOCUMENTS

2013/0169646 A1 7/2013 Yokobori et al.
2018/0253830 A1* 9/2018 Courtney .................. G06T 5/70
(Continued)

FOREIGN PATENT DOCUMENTS

CN 105310726 A 2/2016
CN 111432731 A 7/2020
(Continued)

OTHER PUBLICATIONS

Huh, Jaeyoung, Shujaat Khan, and Jong Chul Ye. "Ot-driven multi-domain unsupervised ultrasound image artifact removal using a single cnn." arXiv preprint arXiv:2007.05205 (2020). (Year: 2020).*

(Continued)

*Primary Examiner* — Chan S Park
*Assistant Examiner* — Paulo Andres Garcia
(74) *Attorney, Agent, or Firm* — Paul Teng

(57) ABSTRACT

A Doppler processing unit or a beam data processing unit generates target time-series data based on a received beam data sequence from a reception unit. An artifact prediction unit predicts the type of artifact to be caused by the target time-series data by inputting the target time-series data to a trained artifact prediction learner. An artifact reduction unit performs artifact reduction processing based on the predicted type of artifact. A display control unit notifies a user of a corrected ultrasound image subjected to the artist reduction processing or the result of the prediction by the artifact prediction unit.

8 Claims, 8 Drawing Sheets

(51) Int. Cl.
G06T 5/70 (2024.01)
G16H 30/40 (2018.01)
(52) U.S. Cl.
CPC .............. *G06T 2207/10132* (2013.01); *G06T 2207/20072* (2013.01); *G06T 2207/20081* (2013.01); *G06T 2207/30004* (2013.01); *G06T 2207/30168* (2013.01)
(58) Field of Classification Search
CPC ..... A61B 8/5269; A61B 8/0891; A61B 8/488; A61B 8/5223; A61B 8/5215; G01S 7/52066; G01S 7/52077; G01S 15/8986
See application file for complete search history.

(56) References Cited

U.S. PATENT DOCUMENTS

| 2020/0107818 | A1 | 4/2020 | Keshet et al. | |
| 2020/0175652 | A1* | 6/2020 | Agarwal | A61B 8/5246 |
| 2021/0077060 | A1* | 3/2021 | Kim | G06N 3/088 |
| 2022/0126190 | A1* | 4/2022 | Kim | A63B 24/0003 |
| 2022/0401081 | A1* | 12/2022 | Sheeran | G01S 7/52046 |
| 2023/0184913 | A1* | 6/2023 | Fraschini | G01S 15/8915 |
| 2024/0177833 | A1* | 5/2024 | Galeotti | G06T 7/10 |

FOREIGN PATENT DOCUMENTS

| CN | 111542853 | A | 8/2020 |
| CN | 111629670 | A | 9/2020 |
| CN | 113491536 | A | 10/2021 |
| JP | H10-243945 | A | 9/1998 |
| JP | 2020-049212 | A | 4/2020 |
| JP | 2020-075104 | A | 5/2020 |
| JP | 2020-081460 | A | 6/2020 |
| JP | 2020-146455 | A | 9/2020 |
| JP | 2021501656 | A | 1/2021 |
| WO | WO2012-008173 | A1 | 1/2012 |

OTHER PUBLICATIONS

B. Luijten et al., "Adaptive Ultrasound Beamforming Using Deep Learning," in IEEE Transactions on Medical Imaging, vol. 39, No. 12, pp. 3967-3978, Dec. 2020, doi: 10.1109/TMI.2020.3008537. (Year: 2020).*
Z. Zhou, Y. Wang, Y. Guo, Y. Qi and J. Yu, "Image Quality Improvement of Hand-Held Ultrasound Devices With a Two-Stage Generative Adversarial Network," in IEEE Transactions on Bio-medical Engineering, vol. 67, No. 1, pp. 298-311, Jan. 2020, doi: 10.1109/TBME.2019.2912986. (Year: 2020).*
Aug. 5, 2025 Japanese official action (and English-language translation thereof) in connection with Japanese Patent Application No. 2022-080338.
Mar. 16, 2026 Chinese official action (and machine translation in English thereof) in connection with Chinese Patent Application No. 2023104477790.

* cited by examiner

TARGET TIME-SERIES DATA

ARTIFACT
PREDICTION
LEARNER

32

ULTRASOUND TIME-SERIES DATA PROCESSING DEVICE AND ULTRASOUND TIME-SERIES DATA PROCESSING PROGRAM

CROSS REFERENCE TO RELATED APPLICATION

This application claims priority to Japanese Patent Application No. 2022-080338 filed on May 16, 2022, which is incorporated herein by reference in its entirety including the specification, claims, drawings, and abstract.

TECHNICAL FIELD

The present specification discloses an ultrasound time-series data processing device and an ultrasound time-series data processing program.

BACKGROUND

Conventionally, ultrasound waves are repeatedly transmitted and received a plurality of times to and from the same position (the same direction as viewed from an ultrasound probe) in a subject, and time-series data which is a time-series received beam data sequence obtained by the repetition is converted into an image or analyzed.

Examples of the image into which the time-series data is converted include an M-mode image in which the horizontal axis indicates time and the vertical axis indicates a depth and in which the state of movement of tissue in the depth direction is indicated by a luminance line extending in the time axis direction, or a Doppler waveform image in which the position of an examined region or the velocity of blood flowing in the examined region is calculated based on the difference between the frequency of the transmitted ultrasound wave and the frequency of the received ultrasound wave and in which the horizontal axis indicates time and the vertical axis indicates the velocity.

WO 2012/008173 A discloses, as a method for analyzing time-series data, a method for determining a vascular disease, particularly arteriosclerosis, vascular stenosis, and an aneurysm, with high accuracy in a non-invasive manner, the method including: receiving a reflected echo whose frequency has changed to $f_0$ by transmitting an ultrasound wave (frequency f) to a blood vessel wall of a beating subject; performing wavelet transformation on the reflected echo to acquire a wavelet spectrum; performing mode decomposition on the wavelet spectrum to acquire a spectrum for each mode; acquiring a waveform for each mode on a time axis by wavelet inverse transformation; calculating a norm value for each mode; and comparing the norm values with a norm distribution obtained from a normal individual to determine the presence or absence of a vascular disease or the morbidity of a specific vascular disease.

Meanwhile, in an ultrasound image into which time-series data are converted, an artifact caused by the time-series data may occur. An artifact in the present specification prevents display of a desired waveform in an ultrasound image into which time-series data have been converted. The artifact may be caused by an operating condition of an ultrasound diagnostic device, a subject, an electric circuit in the ultrasound diagnostic device, or the like. Examples of the artifact include folding (aliasing) in a Doppler waveform image, clutter caused by an unnecessary signal caused by body motion of the subject, a mirror effect caused by saturation of Doppler data, and electrical noise generated from an electric circuit of the ultrasound diagnostic device in a Doppler waveform image and an M-mode image.

An object of the ultrasound time-series data processing device disclosed in the present specification is to generate an ultrasound image that includes a reduced artifact and is based on time-series data. Alternatively, an object of the ultrasound time-series data processing device disclosed in the present specification is to allow a user to easily grasp the type of artifact occurring in an ultrasound image based on time-series data.

SUMMARY OF THE INVENTION

An ultrasound time-series data processing device disposed in the present specification includes: an artifact prediction unit that inputs target time-series data to an artifact prediction learner and predicts a type of artifact to be caused by the target time-series data on the basis of an output of the artifact prediction learner in response to the input, the artifact prediction learner being trained to predict and output the type of artifact to be caused by the time-series data on the basis of the input time-series data, the target time-series data being the time-series data generated by repeatedly transmitting and receiving ultrasound waves a plurality of times at the same position in a target examined region, using, as learning data, a combination of learning time-series data which are time-series data that have been generated based on a reflected wave from an examined region or blood flowing in the examined region by repeatedly transmitting and receiving ultrasound waves a plurality of times to and from the same position in the examined region, indicate a change in a signal over time, and cause the artifact to occur in an ultrasound image based on the time-series data and information indicating the type of artifact; an artifact reduction unit that performs artifact reduction processing for reducing the artifact based on the type of artifact predicted by the artifact prediction unit; and a display control unit that causes a display unit to display an ultrasound image on which the artifact reduction processing has been performed and that is based on the target time-series data.

According to this configuration, after the artifact prediction unit predicts the type of artifact to be caused in the ultrasound image by the target time-series data, the artifact reduction unit performs the artifact reduction processing based on the predicted type of artifact. This reduces the artifact in the ultrasound image based on the target time-series data.

As the artifact reduction processing, the artifact reduction unit may generate an ultrasound image in which the artifact is reduced by inputting the target time-series data to an image generation model that generates an ultrasound image in which the artifact is reduced on the basis of the time-series data that cause the artifact to occur.

According to the configuration, even when the artifact caused in the ultrasound image by the target time-series data cannot be reduced by changing the setting of the ultrasound diagnostic device, it is possible to generate the ultrasound image in which the artifact is reduced, by inputting the target time-series data to the trained image generation model.

The ultrasound time-series data processing device may further include a notification unit that notifies a user that the artifact reduction processing has been performed.

According to this configuration, the user can easily grasp that the artifact reduction processing has been performed on the ultrasound image.

The ultrasound time-series data processing device disposed in the present specification may further include a time-series data generation unit that generates the target time-series data, the artifact prediction unit may predict the type of artifact to be caused by the target time-series data in real time in response to the generation of the target time-series data by the time-series data generation unit, the artifact reduction unit may perform the artifact reduction processing in real time in response to the prediction of the type of artifact by the artifact prediction unit, and the display control unit causes the display unit to display the ultrasound image on which the artifact reduction processing has been performed and that is based on the target time-series data in real time in response to the artifact reduction processing.

In the ultrasound time-series data processing device disclosed in the present specification, the artifact prediction unit can predict the type of artifact to be caused by the target time-series data only by inputting the target time-series data to the trained artifact prediction learner. That is, the amount of calculation for predicting the type of artifact to be caused by the target time-series data can be suppressed to a low level, and thus the type of artifact to be caused by the target time-series data can be predicted at a higher speed. Therefore, in a case where an ultrasound image with a reduced artifact is displayed in real time as in the configuration, it is possible to reduce the delay in the display of the ultrasound image from the time when the target time-series data is acquired.

An ultrasound time-series data processing device disclosed in the present specification includes: an artifact prediction unit that inputs target time-series data to an artifact prediction learner and predicts a type of artifact to be caused by the target time-series data on the basis of an output of the artifact prediction learner in response to the input, the artifact prediction learner being trained to predict and output the type of artifact to be caused by the time-series data on the basis of the input time-series data, the target time-series data being the time-series data generated by repeatedly transmitting and receiving ultrasound waves a plurality of times to the same position in a target examined region, using, as learning data, a combination of learning time-series data which are time-series data that have been generated based on a reflected wave from an examined region or blood flowing in the examined region by repeatedly transmitting and receiving ultrasound waves a plurality of times to and from the same position in the examined region, indicate a change in a signal over time, and cause the artifact to occur in an ultrasound image based on the time-series data and information indicating the type of the artifact; and a notification unit that notifies a user of a result of the prediction by the artifact prediction unit.

According to this configuration, the user can easily grasp the type of artifact to be caused in the ultrasound image by the target time-series data.

The ultrasound time-series data processing device disposed in the present specification may further include a time-series data generation unit that generates the target time-series data, the artifact prediction unit may predict the type of artifact to be caused by the target time-series data in real time in response to the generation of the target time-series data by the time-series data generation unit, and the notification unit may notify the user of the result of the prediction by the artifact prediction unit in real time in response to the prediction of the type of artifact by the artifact prediction unit.

In the ultrasound time-series data processing device disclosed in the present specification, as the artifact reduction processing, even in a case where an ultrasound image with a reduced artifact is newly generated, it is possible to generate an ultrasound image with a reduced artifact only by inputting the target time-series data to the image generation model. That is, the amount of calculation for generating a corrected ultrasound image can be suppressed to a low level, whereby the corrected ultrasound image can be generated at a higher speed. In addition, in a case where the setting of the ultrasound diagnostic device is changed as the artifact reduction processing, changing the setting does not take time. Therefore, in a case where the user is notified of a result of the prediction of the type of artifact in real time as in the configuration, it is possible to reduce the delay in the notification of the prediction result from the time when the target time-series data are acquired.

The target examined region and the examined region may be pulsating regions, and the target time-series data and the learning time-series data may be the time-series data corresponding to the same period in the pulsation cycle of the target examined region and the examined region.

According to this configuration, since the period of the learning time-series data and the period of the target time-series data in the pulsation period are the same, the output accuracy of the artifact prediction learner is improved, and thus, it is possible to improve the accuracy of the prediction of the type of artifact indicated by the target time-series data.

In addition, an ultrasound time-series data processing program disclosed in the present specification causes a computer to function as: an artifact prediction unit that inputs target time-series data to an artifact prediction learner and predicts a type of artifact to be caused by the target time-series data on the basis of an output of the artifact prediction learner in response to the input, the artifact prediction learner being trained to predict and output the type of artifact to be caused by the time-series data on the basis of the input time-series data, the target time-series data being time-series data generated by repeatedly transmitting and receiving ultrasound waves a plurality of times to the same position in a target examined region; an artifact reduction unit that performs artifact reduction processing for reducing the artifact based on the type of artifact predicted by the artifact prediction unit, using, as learning data, a combination of learning time-series data which are time-series data that have been generated based on a reflected wave from an examined region or blood flowing in the examined region by repeatedly transmitting and receiving ultrasound waves a plurality of times to and from the same position in the examined region, indicate a change in a signal over time, and cause the artifact to occur in an ultrasound image based on the time-series data and information indicating the type of artifact; and a display control unit 24 that causes a display unit to display an ultrasound image on which the artifact reduction processing has been performed and that is based on the target time-series data.

In addition, an ultrasound time-series data processing program disclosed in the present specification causes a computer to function as: an artifact prediction unit that inputs target time-series data to an artifact prediction learner and predicts a type of artifact to be caused by the target time-series data on the basis of an output of the artifact prediction learner in response to the input, the artifact prediction learner being trained to predict and output the type of artifact to be caused by the time-series data on the basis of the input time-series data, the target time-series data being the time-series data generated by repeatedly transmitting and receiving ultrasound waves a plurality of times to the same position in a target examined region, using, as learning data, a combination of learning time-series data which are time-series data that have been generated based on a reflected wave from an examined region or blood flowing in the examined region by repeatedly transmitting and receiving ultrasound waves a plurality of times to and from the same position in the examined region, indicate a change in a signal over time, and cause the artifact to occur in an ultrasound image based on the time-series data and information indicating the type of artifact; and a notification unit that notifies a user of the result of the prediction by the artifact prediction unit.

According to the ultrasound time-series data processing device disclosed in the present specification, it is possible to generate an ultrasound image based on time-series data with a reduced artifact. Alternatively, according to the ultrasound time-series data processing device disclosed in the present specification, a user can easily grasp the type of artifact occurring in an ultrasound image based on time-series data.

BRIEF DESCRIPTION OF DRAWINGS

Embodiment(s) of the present disclosure will be described based on the following figures, wherein.

DESCRIPTION OF EMBODIMENTS

Figure 1:
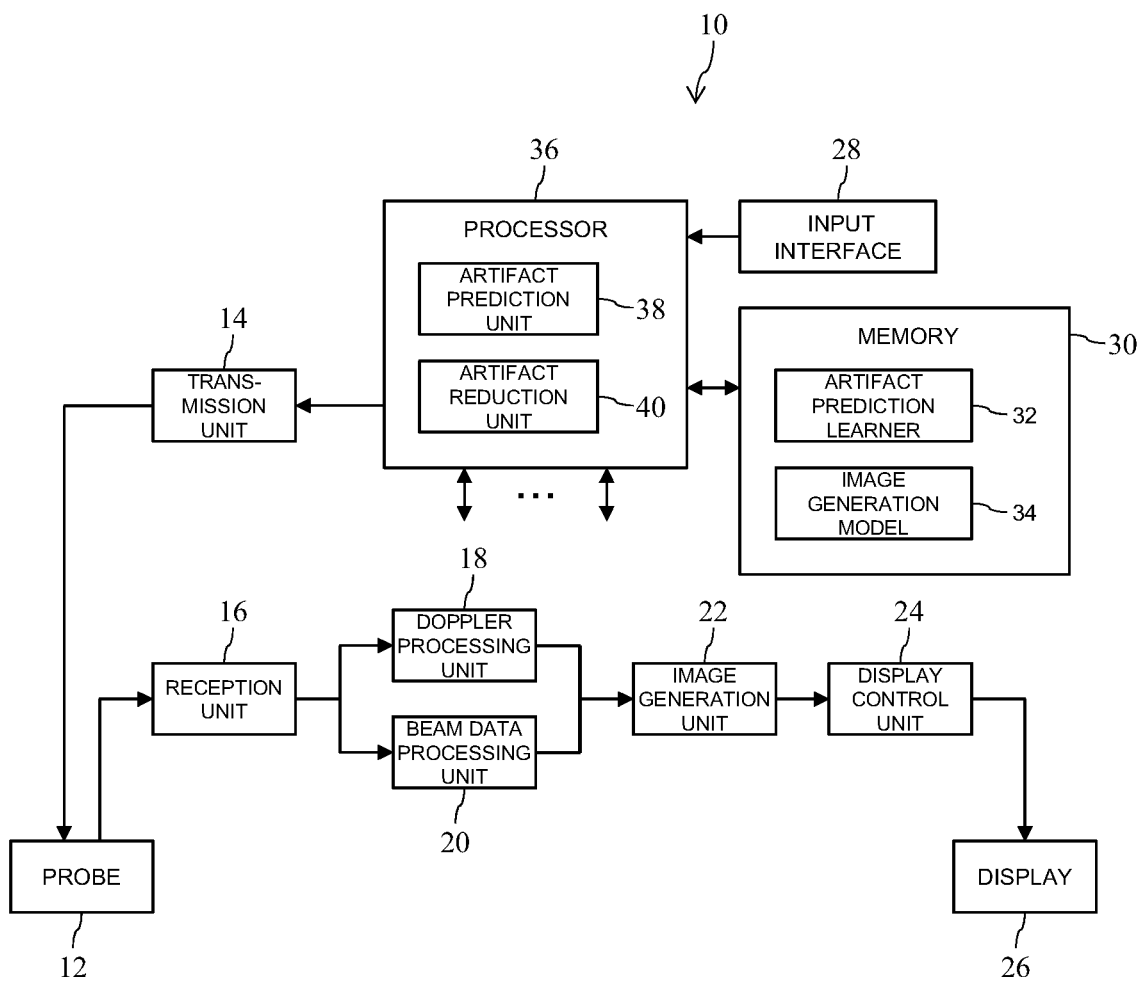
FIG. 1 is a block diagram of an ultrasound diagnostic device according to the present embodiment.

FIG. 1 is a block diagram of an ultrasound diagnostic device 10 as an ultrasound time-series data processing device according to the present embodiment. The ultrasound diagnostic device 10 is a medical device installed in a medical institution such as a hospital and is used for ultrasound inspection.

The ultrasound diagnostic device 10 is operable in a plurality of operation modes including a B mode, a Doppler mode, and an M mode. The B mode is a mode for generating and displaying a tomographic image (B-mode image) in which the amplitude intensity of a reflected wave from a scanned surface is converted into luminance on the basis of received frame data including a plurality of pieces of received beam data obtained by scanning with an ultrasound beam (transmission beam). The Doppler mode is a mode for generating and displaying a waveform (Doppler waveform) indicating the motion speed of tissue in an observation line, based on the difference between the frequency of a transmitted wave and the frequency of a reflected wave in the observation line set in a subject. The Doppler mode may include a continuous wave mode, a pulsed Doppler mode, a color Doppler mode, or a tissue Doppler mode. The M mode is a mode for generating and displaying an M-mode image representing tissue movement on the observation line set in the subject, based on received beam data corresponding to the observation line. The present embodiment particularly focuses on a case where the ultrasound diagnostic device operates in the Doppler mode or the M mode.

A probe 12, which is an ultrasound probe, is a device that transmits an ultrasound wave and receives a reflected wave. Specifically, the probe 12 is brought into contact with the body surface of the subject, transmits an ultrasound wave toward the subject, and receives a wave reflected on tissue in the subject. A vibration element array including a plurality of vibration elements is provided in the probe 12. A transmission signal that is an electric signal is supplied from a transmission unit 14 to be described later to each of the vibration elements included in the vibration element array, whereby an ultrasound beam (transmission beam) is generated. In addition, each of the vibration elements included in the vibration element array receives a reflected wave from the subject, converts the reflected wave into a reception signal that is an electric signal, and transmits the reception signal to a reception unit 16 to be described later.

In order to transmit an ultrasound wave, the transmission unit 14 supplies a plurality of transmission signals to the probe 12 (specifically, the vibration element array) in parallel under the control by a processor 36 to be described later. As a result, the ultrasound wave is transmitted from the vibration element array.

In the Doppler mode or the M mode, the transmission unit 14 supplies the transmission signals to the probe 12 so that the probe 12 repeatedly transmits the transmission beam a plurality of times to the same position in an examined region of the subject determined by a user such as a doctor or a medical technician. In other words, the transmission unit 14 supplies the transmission signals to the probe 12 so that the probe 12 repeatedly transmits the transmission beam in a direction toward the same position in the examined region a plurality of times. In the B mode, the transmission unit 14 supplies the transmission signals to the probe 12 so that a scanning surface is electronically scanned with the transmission beam transmitted from the probe 12. Alternatively, time-division scanning may be performed to repeat transmission of the transmission beam to the same position determined by the user while the scanning surface is electronically scanned with the transmission beam.

At the time of receiving the reflected wave, the reception unit 16 receives a plurality of reception signals from the probe 12 (specifically, the vibration element array) in parallel. The reception unit 16 performs phasing addition (delay addition) on the plurality of reception signals, thereby generating received beam data.

In the Doppler mode or the M mode, the probe 12 repeats the transmission of the transmission beam to the same position in the examined region a plurality of times, so that the reception unit 16 receives a plurality of reflected waves from the examined region or blood flowing in the examined region, and generates a time-series received beam data sequence based on the plurality of reflected waves. In the B mode, the reception unit 16 configures the received frame data according to the plurality of pieces of received beam data arranged in the scanning direction.

Figure 2:
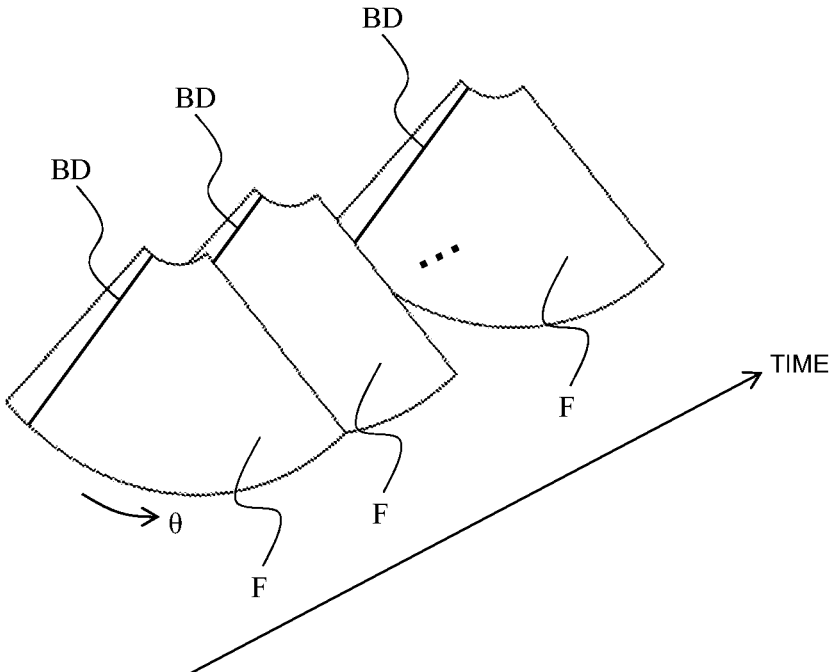
FIG. 2 is a conceptual diagram illustrating a relationship between received beam data and received frame data.

FIG. 2 is a conceptual diagram illustrating a relationship between the received beam data BD and received frame data F. In the Doppler mode or the M mode, ultrasound waves are transmitted and received to and from a position (direction) designated by the user. As a result, a plurality of time-series pieces of received beam data BD (that is, received beam data sequence) are generated. The received beam data BD include information indicating the intensities and frequencies of the reflected waves from each depth. In the B mode, the scanning is performed with the transmission beam in the scanning direction θ, and the received frame data F is generated according to the plurality of pieces of received beam data arranged in the scanning direction θ.

In the Doppler mode, the received beam data sequence is transmitted to a Doppler processing unit 18. In the M mode, the received beam data sequence is transmitted to a beam data processing unit 20.

Returning to FIG. 1, the Doppler processing unit 18 generates Doppler data as time-series data indicating a change over time in the position of the examined region or a change over time in the velocity of the blood flowing in the examined region on the basis of the received beam data sequence from the reception unit 16 in the Doppler mode. Specifically, the Doppler processing unit 18 generates Doppler data by performing processing such as quadrature detection of multiplying received beam data by a reference frequency and extracting a Doppler shift through a low-pass filter, sample gate processing of extracting only a signal at a position of a sample volume (in the pulse Doppler mode), A/D conversion of a signal, and frequency analysis by a fast Fourier transform method (FFT method). The generated Doppler data are transmitted to an image generation unit 22 and the processor 36. In the Doppler mode, the reception unit 16 and the Doppler processing unit 18 correspond to a time-series data generation unit.

In the M mode, the beam data processing unit 20 performs various types of signal processing such as gain correction processing, logarithmic amplification processing, and filter processing on the received beam data sequence from the reception unit 16. The processed received beam data sequence is transmitted to the image generation unit 22 and the processor 36. In the present embodiment, in the M mode, the received beam data sequence processed by the beam data processing unit 20 corresponds to the time-series data indicating the change over time in the position of the examined region. In this case, the reception unit 16 and the beam data processing unit 20 correspond to a time-series data generation unit. Note that also in the B mode, the beam data processing unit 20 performs the above-described various types of signal processing on the received frame data from the reception unit 16.

The image generation unit 22 includes a digital scan converter, and includes a coordinate conversion function, a pixel interpolation function, a frame rate conversion function, and the like.

In the Doppler mode, the image generation unit 22 generates a Doppler waveform image on the basis of the Doppler data from the Doppler processing unit 18. The Doppler waveform is a waveform indicated on a two-dimensional plane of time and velocity, and indicates a change over time in the position of the examined region or a change over time in the velocity of the blood flowing in the examined region on the observation line corresponding to the received beam data sequence.

In the M mode, the image generation unit 22 generates an M-mode image on the basis of the received beam data sequence from the beam data processing unit 20. The M-mode image is a waveform indicated on a two-dimensional plane of time and depth, and indicates a change over time in the position of the examined region on the observation line corresponding to the received beam data sequence.

An artifact may occur in an ultrasound image (Doppler waveform image or M-mode image) generated by the image generation unit 22 on the basis of time-series data (Doppler data or received beam data sequence after signal processing). As described above, an artifact in the present specification prevents display of a desired waveform in an ultrasound image into which time-series data are converted, and includes, for example, folding or a mirror effect caused by an operating condition (setting) of the ultrasound diagnostic device 10, clutter caused by a subject, electrical noise caused by an electrical circuit in the ultrasound diagnostic device, or the like. For example, when the clutter is caused by the movement of the heart valve, the clutter has a wide range of components from high-speed to low-speed components, and appears as a bright line substantially parallel to the vertical axis in a Doppler waveform image in which the horizontal axis indicates time and the vertical axis indicates speed. In addition, for example, when the clutter is caused by the movement of the heart wall, the clutter has a low-speed component with a high signal intensity, and appears as a bright line extending in the lateral direction in the vicinity of a line with a speed of 0 in a Doppler waveform image in which the horizontal axis indicates time and the vertical axis indicates speed. Of course, the types of artifacts are not limited to the above types.

Note that, in the B-mode, the image generation unit 22 generates, on the basis of the received frame data from the beam data processing unit 20, a B-mode image in which the amplitude (intensity) of a reflected wave is represented by luminance.

The display control unit 24 causes a display 26 as a display unit including, for example, a liquid crystal panel or the like to display various images such as a Doppler waveform image, an M-mode image, or a B-mode image generated by the image generation unit 22. In addition, the display control unit 24 causes the display 26 to display an ultrasound image that is a prediction result of an artifact prediction unit 38 to be described later or a processing result of an artifact reduction unit 40 to be described later.

Note that each of the transmission unit 14, the reception unit 16, the Doppler processing unit 18, the beam data processing unit 20, the image generation unit 22, and the display control unit 24 includes one or a plurality of processors, chips, electric circuits, and the like. Each of the units may be implemented by cooperation of hardware and software.

An input interface 28 includes, for example, a button, a track ball, a touch panel, or the like. The input interface 28 is for inputting a user's instruction to the ultrasound diagnostic device 10.

A memory 30 includes a hard disk drive (HDD), a solid state drive (SSD), an embedded multimedia card (eMMC), a read only memory (ROM), a random access memory (RAM), or the like. The memory 30 stores an ultrasound time-series data processing program for operating each unit of the ultrasound diagnostic device 10. Note that the ultrasound time-series data processing program can also be stored in a computer-readable non-transitory storage medium such as a universal serial bus (USB) memory or a CD-ROM. The ultrasound diagnostic device 10 or another computer can read and execute the ultrasound time-series data processing program from such a storage medium. Furthermore, as illustrated in FIG. 1, an artifact prediction learner 32 and an image generation model 34 are stored in the memory 30.

The artifact prediction learner 32 includes, for example, a learning model such as a recurrent neural network (RNN), a long short term memory (LSTM) which is a type of RNN, a convolutional neural network (CNN), or a deep Q-network (DQN) using a deep reinforcement learning algorithm. The artifact prediction learner 32 is trained to predict and output the type of artifact to be caused by the time-series data on the basis of the input time-series data, using, as learning data, a combination of learning time-series data which are time-series data that have been generated based on a reflected wave from an examined region or blood flowing in the examined region by repeatedly transmitting and receiving ultrasound waves a plurality of times to and from the same position in the examined region and causes an artifact to occur in an ultrasound image based on the time-series data and information (label) indicating the type of artifact.

Figure 3:
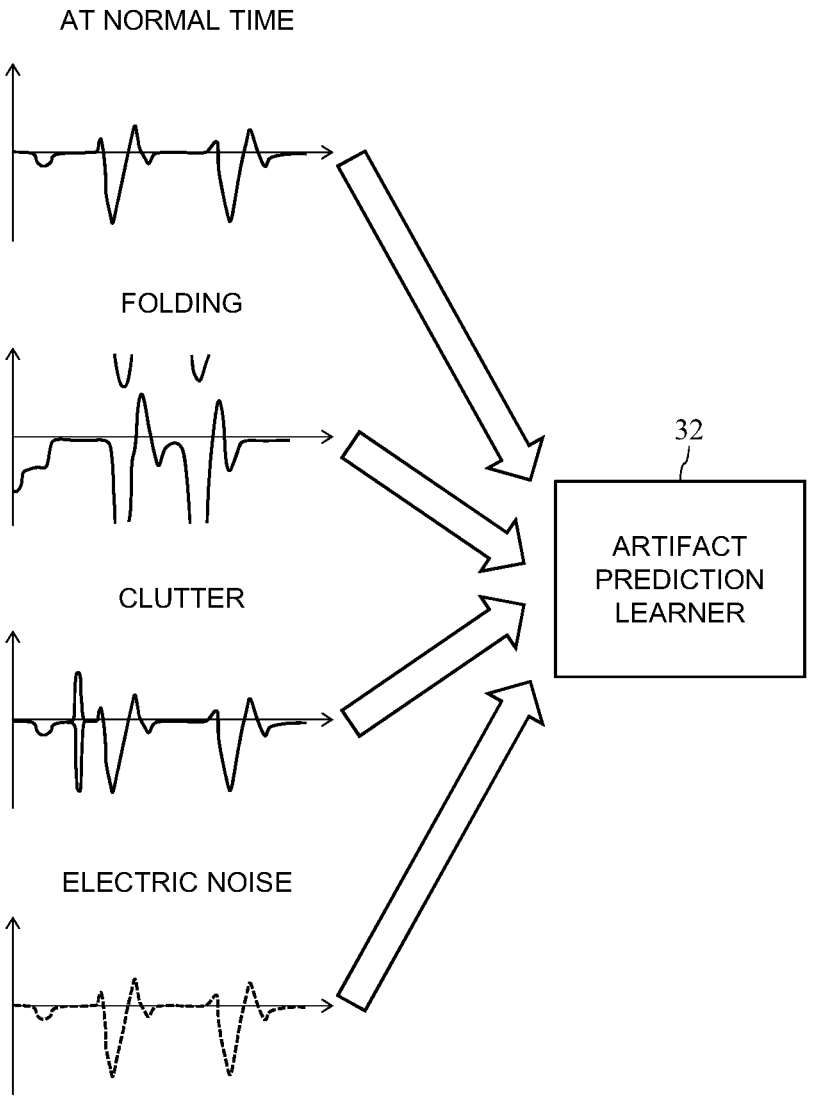
FIG. 3 is a conceptual diagram illustrating a state of processing of training an artifact prediction learner.

FIG. 3 is a conceptual diagram illustrating a state of processing of training the artifact prediction learner 32. For example, learning time-series data that cause "folding" as the type of artifact to occur in a Doppler waveform image are input to the artifact prediction learner 32. In this case, the artifact prediction learner 32 predicts and outputs the artifact to be caused by the learning time-series data. An activation function such as a softmax function may be provided in the last stage (output layer) of the artifact prediction learner 32, and the artifact prediction learner 32 may output, as output data, the possibility (probability) that the learning time-series data may cause an artifact to occur for each of a plurality of types of artifacts. A computer that performs training processing calculates an error between the output data and a label (in this case, "folding") attached to the learning time-series data according to a predetermined loss function, and adjusts each parameter (for example, a weight or a bias of each neuron) of the artifact prediction learner 32 so as to reduce the error. By repeating such training processing, the artifact prediction learner 32 can predict and output the type of artifact to be caused by the time-series data on the basis of the input time-series data.

The examined region to be a target of the learning time-series data may be a pulsating region. In this case, the learning time-series data may be data corresponding to a predetermined period in the pulsation cycle of the examined region. For example, an electrocardiographic waveform of the subject may be acquired from an electrocardiograph attached to the subject, and time-series data based on a received beam data sequence acquired in a period between R waves in the electrocardiographic waveform may be used as learning time-series data.

In the present embodiment, the learning time-series data are data (corresponding to the Doppler data or the received beam data sequence described above) before image conversion, but the learning time-series data may be a Doppler waveform image or an M-mode image (specifically, data obtained by quantifying the features of the Doppler waveform image or the M-mode image) generated on the basis of the Doppler data or the received beam data sequence.

Note that, in FIG. 3, time-series data (normal time) that do not cause an artifact are included as the learning data, but it may be the case that the time-series data at the normal time are not included in the learning data. In addition, in the artifact prediction learner 32, another learner may be prepared for each type of artifact. In that case, each learner is trained to output a probability that the input time-series data indicate a corresponding type of artifact.

In the present embodiment, the artifact prediction learner 32 is trained by another computer other than the ultrasound diagnostic device 10, and the trained artifact prediction learner 32 is stored in the memory 30. However, the processing of training the artifact prediction learner 32 may be performed by the ultrasound diagnostic device 10 using the time-series data acquired by the ultrasound diagnostic device 10 as the learning time-series data. In this case, the processor 36 functions as a training processing unit that performs the processing of training the artifact prediction learner 32.

The image generation model 34 is a learning model that uses a latent variable as an input and generates a two-dimensional image based on the latent variable. The image generation model 34 includes, for example, a generative adversarial network (GAN) or the like. The GAN includes a set of an image generator that generates a two-dimensional image based on the latent variable and an image discriminator that discriminates whether an image to be discriminated is an image generated by the image generator. The image discriminator is trained to be able to discriminate whether an image to be discriminated is a generated image with higher accuracy. For example, the image discriminator is trained using, as learning data, a combination of a generated image and information (label) indicating that the image is a generated image, and a combination of a true image (an image that is not a generated image) and information indicating that the image is a true image. On the other hand, the image generator is trained to generate an image that is close to a real image so as to deceive the image discriminator (the image discriminator erroneously discriminates). For example, the image generator is trained such that an image generated based on the latent variable is determined to be a true image by the image discriminator. The sufficiently trained GAN (specifically, the image generator included in the GAN) can generate a more realistic image.

In the present embodiment, the image generation model 34 is trained to use, as a latent variable (input data), time-series data that cause an artifact to occur so as to generate, from the latent variable, an ultrasound image (specifically, a Doppler waveform image or an M-mode image) in which the artifact is reduced and that is based on the time-series data. For example, the image generation model 34 is trained to use, as input data, time-series data that cause clutter to occur so as to generate an ultrasound image in which the clutter is reduced.

Returning to FIG. 1, the processor 36 includes at least one of a general-purpose processing device (for example, a central processing unit (CPU) or the like) and a dedicated processing device (for example, a graphics processing unit (GPU), an application specific integrated circuit (ASIC), or a field-programmable gate array (FPGA), a programmable logic device, or the like). The processor 36 may be configured by cooperation of a plurality of processing devices present at physically separated positions, instead of one processing device. As illustrated in FIG. 1, the processor 36 functions as an artifact prediction unit 38 and an artifact reduction unit 40 according to the ultrasound time-series data processing program stored in the memory 30.

Figure 4:
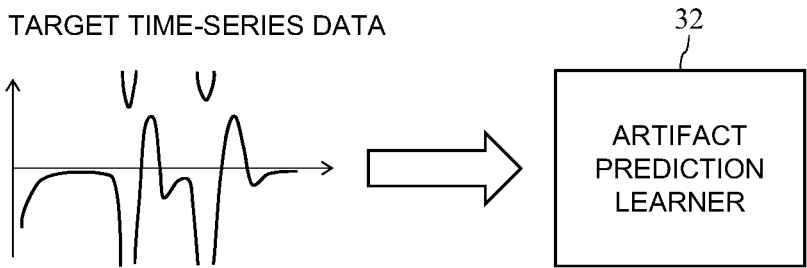
FIG. 4 is a conceptual diagram illustrating a state of prediction processing using the artifact prediction learner.

FIG. 4 is a conceptual diagram illustrating a state of prediction processing using the artifact prediction learner 32. The artifact prediction unit 38 inputs, to the trained artifact prediction learner 32, time-series data (referred to as "target time-series data" in the present specification) obtained by repeatedly transmitting and receiving ultrasound waves a plurality of times to and from the same position in a target examined region. Note that the target examined region is a region of the target subject to and from which ultrasound waves are transmitted and received in order to acquire the target time-series data (time-series data from which the type of artifact to be caused by the time-series data is predicted). As described above, the target time-series data are generated by the reception unit 16 and the Doppler processing unit 18 (in the Doppler mode) or by the reception unit 16 and the beam data processing unit 20

(in the M mode). Furthermore, the target time-series data may be a Doppler waveform image or an M-mode image (specifically, data obtained by quantifying the features of the Doppler waveform image and the M-mode image) obtained on the basis of the Doppler data or the received beam data sequence.

The artifact prediction learner 32 predicts the type of artifact to be caused by the target time-series data on the basis of the input target time-series data, and outputs output data indicating the prediction result. The artifact prediction unit 38 predicts the type of artifact to be caused by the target time-series data on the basis of the output data of the artifact prediction learner 32. In a case where the artifact prediction learner 32 outputs, as the output data, the possibility that the target time-series data may cause an artifact to occur for each of a plurality of types of artifacts, the artifact prediction unit 38 can predict the possibility that the target time-series data may cause an artifact to occur for each of the plurality of types of artifacts.

In a case where a plurality of artifact prediction learners 32 are prepared for each type of artifact, the artifact prediction unit 38 sequentially transmits the target time-series data to the plurality of artifact prediction learners 32, and predicts the possibility that the target time-series data may cause an artifact to occur for each of the plurality of types of artifacts on the basis of output data of each of the plurality of artifact prediction learners 32.

When the target examined region and the examined region that is the target of the learning time-series data are pulsating regions, the target time-series data and the learning time-series data may be time-series data corresponding to the same period in the pulsation cycle of the target examined region and the examined region. For example, when the learning time-series data are time-series data based on a received beam data sequence acquired in a period between R waves in an electrocardiographic waveform, the artifact prediction unit 38 may also set the target time-series data as time-series data based on the received beam data sequence acquired in the period between the R waves in the electrocardiographic waveform. Since the period of the learning time-series data and the period of the target time-series data in the pulsation cycle are the same, it is possible to improve the output accuracy of the artifact prediction learner 32. That is, the accuracy of the prediction of the type of artifact to be caused by the target time-series data by the artifact prediction unit 38 is improved.

The artifact reduction unit 40 performs artifact reduction processing for reducing the artifact on the basis of the type of artifact predicted by the artifact prediction unit 38.

When the artifact caused in the ultrasound image by the target time-series data can be reduced by changing the operating condition (setting) of the ultrasound diagnostic device 10, the artifact reduction unit 40 performs processing of changing the setting of the ultrasound diagnostic device 10 as the artifact reduction processing.

For example, in a case where the type of artifact predicted by the artifact prediction unit 38; that is, the type of artifact caused by the target time-series data is "folding," the artifact reduction unit 40 performs 0 shift of vertically shifting the 0 Hertz line of the Doppler waveform so as to eliminate the folding. Alternatively, the artifact reduction unit adjusts the pulse repetition frequency (PRF) to eliminate the folding. Furthermore, in a case where the type of artifact predicted by the artifact prediction unit 38 is a "mirror effect," the artifact reduction unit 40 performs processing of adjusting a gain so as to reduce the mirror effect. Furthermore, in a case where the type of artifact predicted by the artifact prediction unit 38 is "electrical noise," the artifact reduction unit 40 performs processing of adjusting the gain so as to reduce the electrical noise.

On the other hand, when the artifact caused in the ultrasound image by the target time-series data cannot be reduced by changing the setting of the ultrasound diagnostic device 10, the artifact reduction unit 40 inputs the target time-series data to the trained image generation model 34 as the artifact reduction processing. The image generation model 34 outputs an ultrasound image based on the target time-series data and having the reduced artifact, based on the target time-series data input as the latent variable. In this way, the ultrasound image with the reduced artifact is generated. Note that the input of the image generation model 34 may be a Doppler waveform image or an M-mode image (specifically, data obtained by quantifying the features of the Doppler waveform image and the M-mode image) obtained on the basis of the target time-series data.

The display control unit 24 notifies the user of the prediction result of the artifact prediction unit 38. That is, the display control unit 24 functions as a notification unit. Note that, in the present embodiment, the prediction result of the artifact prediction unit 38 is displayed on the display 26 by the display control unit 24 as described below, but in addition to or instead of this, the prediction result of the artifact prediction unit 38 may be notified to the user by voice output or the like.

Figure 5:
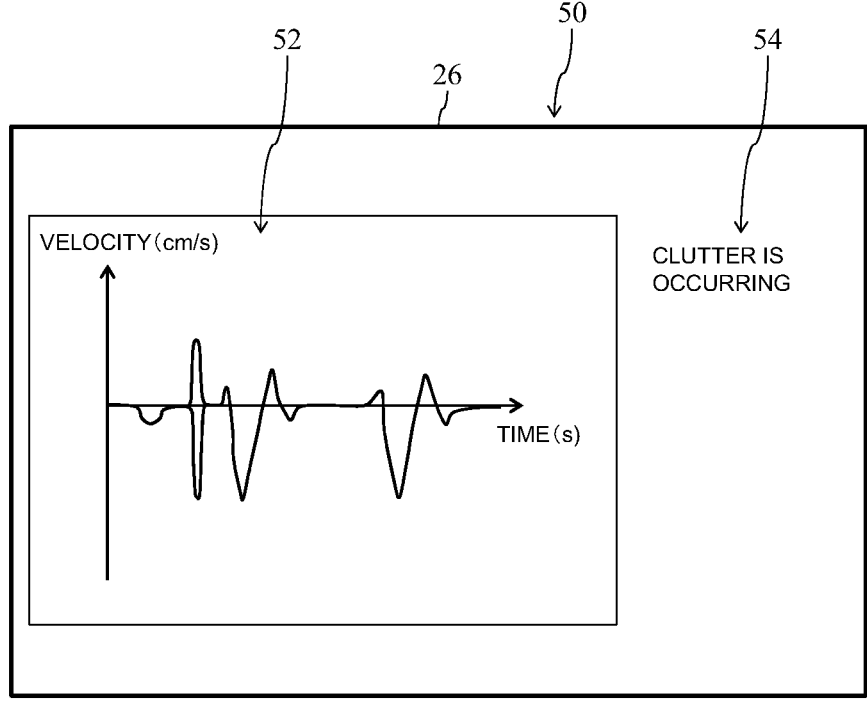
FIG. 5 is a diagram illustrating an example of a notification screen for notifying a prediction result of an artifact prediction unit.

FIG. 5 is a diagram illustrating an example of a notification screen 50 for notifying the prediction result of the artifact prediction unit 38 displayed on the display 26. The notification screen 50 displays an ultrasound image 52 generated on the basis of the target time-series data and a prediction result 54 of the artifact prediction unit 38; that is, the type of artifact predicted to be caused by the target time-series data. Note that the notification screen 50 is in the Doppler mode, and the Doppler waveform image is displayed as the ultrasound image 52. However, of course, in the M mode, the M mode image is displayed as the ultrasound image 52.

In a case where the artifact prediction unit 38 predicts the possibility that the target time-series data corresponds to each of the plurality of types of artifacts, the display control unit 24 may notify the user of the possibility that the target time-series data corresponds to each of the plurality of types of artifacts.

As described above, when the prediction result of the artifact prediction unit 38 is notified to the user, the user can easily grasp whether or not an artifact occurs and the type of artifact that has occurred in the ultrasound image 52 based on the target time-series data. In particular, it may be difficult for a user who is unfamiliar with viewing the ultrasound image 52 to determine whether an artifact occurs in the displayed ultrasound image 52. For such a user, it is particularly useful to notify whether or not an artifact occurs in the displayed ultrasound image 52 or the prediction of the type of artifact.

Figure 6:
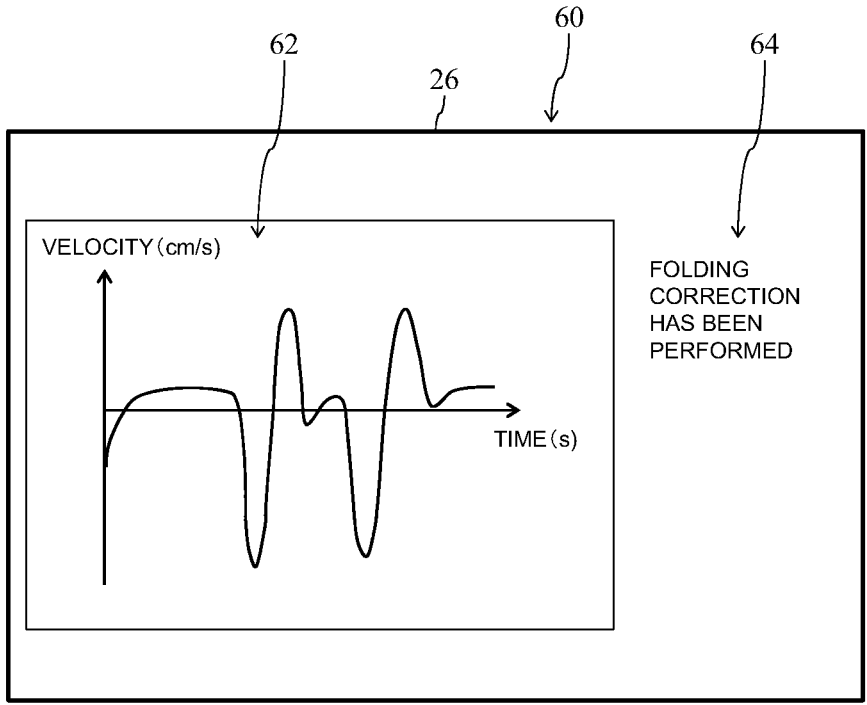
FIG. 6 is a diagram illustrating a first display example of an ultrasound image with a reduced artifact.
Figure 7:
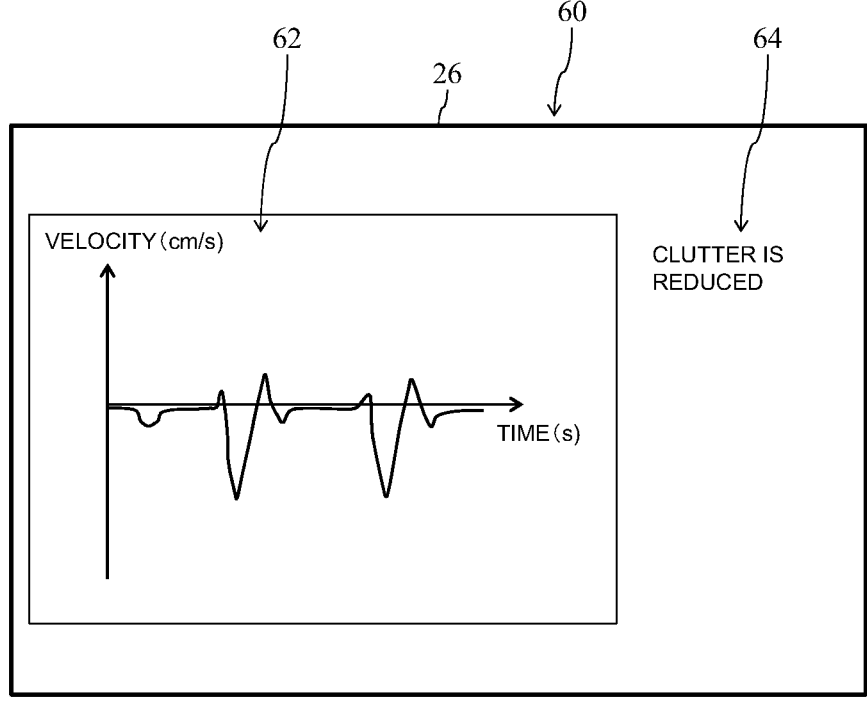
FIG. 7 is a diagram illustrating a second display example of an ultrasound image with a reduced artifact.

FIGS. 6 and 7 illustrate a display screen 60 including a corrected ultrasound image 62 with reduced artifacts displayed on the display 26. In a case where the artifact reduction unit 40 performs the artifact reduction processing described above, the display control unit 24 causes the display 26 to display the corrected ultrasound image 62 on which the artifact reduction processing has been performed and that is based on the target time-series data.

For example, in the example illustrated in FIG. 6, the display control unit 24 displays the corrected ultrasound image 62 in which folding has been eliminated by the 0 shift and that is an ultrasound image based on the target time-series data that causes folding to occur. In a case where the image generation by the image generation model 34 is performed as the artifact reduction processing, the display control unit 24 displays the corrected ultrasound image 62 generated by the image generation model 34 as illustrated in FIG. 7.

In addition to the corrected ultrasound image 62, the display control unit 24 may notify the user that the artifact reduction processing has been performed on the corrected ultrasound image 62. Furthermore, the display control unit 24 may notify the user of the type of artifact reduced by the artifact reduction processing. For example, in the corrected ultrasound image 62 illustrated in FIG. 6, since the folding is eliminated, the display control unit 24 displays a notification message 64 notifying that the folding correction (specifically, 0 shift) has been performed on the corrected ultrasound image 62. Similarly, since the clutter is reduced in the corrected ultrasound image 62 illustrated in FIG. 7, the display control unit 24 displays the notification message 64 notifying that the clutter is reduced.

As a result, the user can easily grasp that the displayed corrected ultrasound image 62 is an image on which the artifact reduction processing has been performed.

As described above, in the present embodiment, the artifact prediction unit 38 can predict the type of artifact to be caused by the target time-series data only by inputting the target time-series data to the trained artifact prediction learner 32. That is, the amount of calculation for predicting the type of artifact to be caused by the target time-series data can be suppressed to a low level, and thus the type of artifact to be caused by the target time-series data can be predicted at a higher speed.

Therefore, the artifact prediction unit 38 may predict the type of artifact to be caused by the target time-series data in real time in response to the generation of the target time-series data, and the display control unit 24 may notify the user of the result of the prediction by the artifact prediction unit 38 in real time in response to the prediction of the type of artifact to be caused by the target time-series data by the artifact prediction unit 38. According to the present embodiment, even if such real-time processing is performed, it is possible to smoothly notify the user of the prediction result of the artifact prediction unit 38 without causing delay or the like.

Furthermore, even in a case where the artifact reduction unit 40 newly generates a corrected ultrasound image as the artifact reduction processing, the artifact reduction unit can generate a corrected ultrasound image with a reduced artifact only by inputting the target time-series data to the image generation model 34. That is, the amount of calculation for generating a corrected ultrasound image can be suppressed to a low level, whereby the corrected ultrasound image can be generated at a higher speed. Note that, in a case where the setting of the ultrasound diagnostic device 10 is changed as the artifact reduction processing, it does not take time to change the setting.

Therefore, the artifact prediction unit 38 may predict the type of artifact to be caused by the target time-series data in real time in response to the generation of the target time-series data, the artifact reduction unit 40 may perform the artifact reduction processing in real time in response to the prediction of the type of artifact by the artifact prediction unit 38, and the display control unit 24 may cause the display 26 to display the corrected ultrasound image 62 based on the target time-series data in real time in response to the artifact reduction processing. According to the present embodiment, even if such real-time processing is performed, the corrected ultrasound image 62 can be smoothly displayed on the display 26 without delay or the like.

Figure 8:
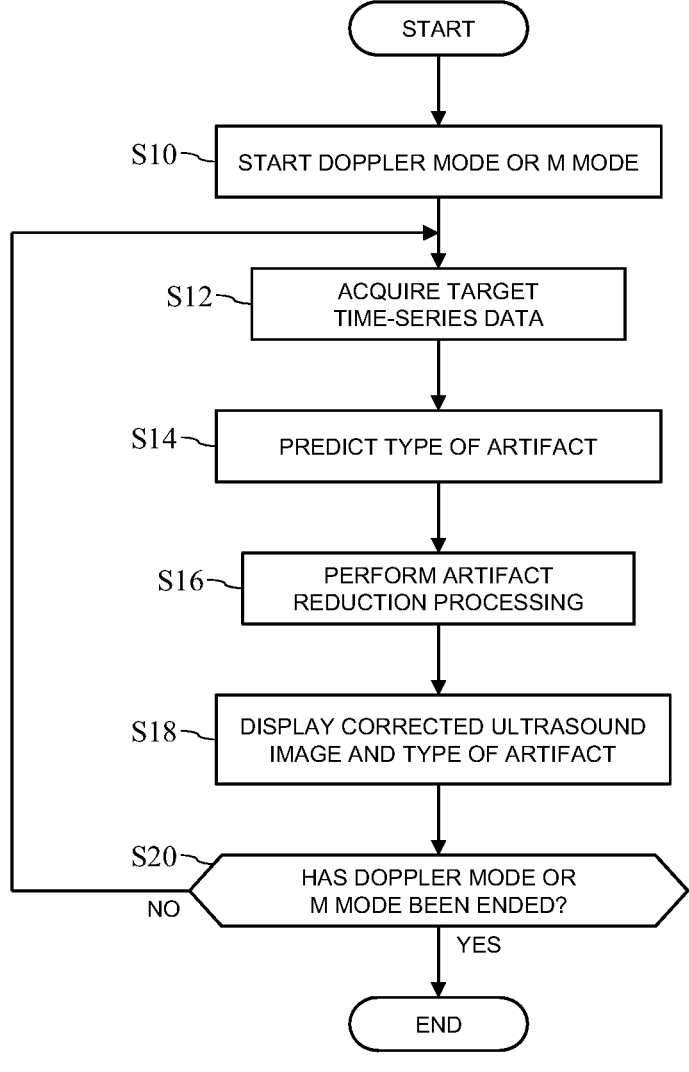
FIG. 8 is a flowchart illustrating a process performed by the ultrasound diagnostic device according to the present embodiment.

Hereinafter, a process performed by the ultrasound diagnostic device 10 according to the present embodiment will be described with reference to a flowchart illustrated in FIG. 8.

In step S10, the ultrasound diagnostic device 10 starts the Doppler mode or the M mode in response to a user's instruction from the input interface 28.

In step S12, in the Doppler mode, the Doppler processing unit 18 generates Doppler data as the target time-series data on the basis of a received beam data sequence from the reception unit 16. In the M mode, the beam data processing unit 20 generates a received beam data sequence subjected to various types of signal processing as the target time-series data.

In step S14, the artifact prediction unit 38 inputs the target time-series data (Doppler data or received beam data sequence) generated in step S12 to the trained artifact prediction learner 32. Then, the artifact prediction unit 38 predicts the type of artifact to be caused by the target time-series data on the basis of output data of the artifact prediction learner 32 for the target time-series data.

In step S16, the artifact reduction unit 40 performs the artifact reduction processing for reducing the artifact on the basis of the type of artifact predicted by the artifact prediction unit 38. Step S16 may be bypassed.

In step S18, the display control unit 24 causes the display 26 to display a corrected ultrasound image on which the artifact reduction processing has been performed in step S16 and the type of the reduced artifact. Note that when step S16 is bypassed, the display control unit 24 notifies the user of the result (the type of artifact occurring in the ultrasound image 52) of the prediction by the artifact prediction unit 38.

In step S20, the processor 36 determines whether or not the Doppler mode or the M mode has been ended according to the user's instruction. When the Doppler mode or the M mode is continued, the process returns to step S12, and the processing from steps S12 to S20 is repeated. When the Doppler mode or the M mode is ended, the process is ended.

Although the ultrasound time-series data processing device according to the present disclosure has been described above, the ultrasound time-series data processing device according to the present disclosure is not limited to the above-described embodiment, and various modifications can be made without departing from the gist thereof.

For example, in the present embodiment, the ultrasound time-series data processing device is the ultrasound diagnostic device 10, but the ultrasound time-series data processing device is not limited to the ultrasound diagnostic device 10, and may be another computer. In this case, the trained artifact prediction learner 32 is stored in a memory accessible from the computer as the ultrasound time-series data processing device, and a processor of the computer functions as the artifact prediction unit 38, the artifact reduction unit 40, and the display control unit 24.

The invention claimed is:

1. An ultrasound time-series data processing device comprising a non-transitory storage medium tangibly embodying one or more programs of instructions, and one or more processors configured to execute the one or more programs of instructions embodied in the non-transitory storage medium, to perform a method comprising:

inputting target time-series data to an artifact prediction learner and predicting a type of artifact to be caused by the target time-series data on the basis of an output of the artifact prediction learner in response to the input, the artifact prediction learner being trained to predict and output the type of artifact to be caused by the time-series data on the basis of the input time-series data, the target time-series data being the time-series data generated by repeatedly transmitting and receiving ultrasound waves a plurality of times to the same position in a target examined region, using, as learning data, a combination of learning time-series data which are time-series data that have been generated based on a reflected wave from an examined region or blood flowing in the examined region by repeatedly transmitting and receiving ultrasound waves a plurality of times to and from the same position in the examined region, indicate a change in a signal over time, and cause the artifact to occur in an ultrasound image based on the time-series data and information indicating the type of the artifact;

performing artifact reduction processing for reducing the artifact based on the predicted type of artifact;

when the type of artifact that is predicted is reducible by changing an operating condition of an ultrasound diagnostic device that generates the target time-series data, changing setting of the ultrasound diagnostic device as the artifact reduction processing;

when the type of artifact that is predicted is unreducible by changing the operating condition of the ultrasound diagnostic device that generates the target time-series data, inputting the target time-series data to an image generation model, as the artifact reduction processing, the image generation model being configured to generate an ultrasound image based on the target time-series data that causes artifact and having reduced artifact, thereby generating an ultrasound image with reduced artifact; and causing a display to display an ultrasound image on which the artifact reduction processing has been performed and that is based on the target time-series data.

2. The ultrasound time-series data processing device according to claim 1, wherein the method performed by the one or more processors further comprises notifying a user that the artifact reduction processing has been performed.

3. The ultrasound time-series data processing device according to claim 1, wherein the method performed by the one or more processors further comprises generating the target time-series data, the type of artifact to be caused by the target time-series data is predicted in real time in response to the generation of the target time-series data, the artifact reduction processing is performed in real time in response to the prediction of the type of artifact, and the ultrasound image on which the artifact reduction processing has been performed and that is based on the target time-series data in real time is displayed in response to the artifact reduction processing.

4. The ultrasound time-series data processing device according to claim 1, wherein the target examined region and the examined region are pulsating regions, and the target time-series data and the learning time-series data are time-series data corresponding to the same period in a pulsation cycle of the target examined region and the examined region.

5. A computer-readable non-transitory storage medium storing a computer-executable command, the command causing a computer to execute:

an artifact prediction step of inputting target time-series data to an artifact prediction learner and predicting a type of artifact to be caused by the target time-series data on the basis of an output of the artifact prediction learner in response to the input, the artifact prediction learner being trained to predict and output the type of artifact to be caused by the time-series data on the basis of the input time-series data, the target time-series data being the time-series data generated by repeatedly transmitting and receiving ultrasound waves a plurality of times to the same position in a target examined region, using, as learning data, a combination of learning time-series data which is time-series data that have been generated based on a reflected wave from an examined region or blood flowing in the examined region by repeatedly transmitting and receiving ultrasound waves a plurality of times to and from the same position in the examined region, indicate a change in a signal over time, and cause the artifact to occur in an ultrasound image based on the time-series data and information indicating the type of the artifact;

an artifact reduction step of performing artifact reduction processing for reducing the artifact based on the type of artifact predicted by the artifact prediction step;

a step of, when the type of artifact that is predicted is reducible by changing an operating condition of an ultrasound diagnostic device that generates the target time-series data, changing setting of the ultrasound diagnostic device as the artifact reduction processing, and when the type of artifact that is predicted is unreducible by changing the operating condition of the ultrasound diagnostic device that generates the target time-series data, inputting the target time-series data to an image generation model, as the artifact reduction processing, the image generation model being configured to generate an ultrasound image based on the target time-series data that causes artifact and having reduced artifact, thereby generating an ultrasound image with reduced artifact; and a display control step of causing an ultrasound image to be displayed on which the artifact reduction processing has been performed and that is based on the target time-series data.

6. The computer-readable non-transitory storage medium according to claim 5, wherein the command additionally causes the computer to execute a step of notifying a user that the artifact reduction processing has been performed.

7. The computer-readable non-transitory storage medium according to claim 5, wherein the type of artifact to be caused by the target time-series data is predicted in real time in response to the generation of the target time-series data, the artifact reduction processing is performed in real time in response to the prediction of the type of artifact, and the ultrasound image on which the artifact reduction processing has been performed and that is based on the target time-series data in real time is displayed in response to the artifact reduction processing.

8. The computer-readable non-transitory storage medium according to claim 5, wherein the target examined region and the examined region are pulsating regions, and the target time-series data and the learning time-series data are time-series data corresponding to the same period in a pulsation cycle of the target examined region and the examined region.

* * * * *